United States Patent [19]

Evers et al.

[11] 4,031,256

[45] * June 21, 1977

[54] FOODSTUFF FLAVOR COMPOSITIONS COMPRISING 3-FURYL ALKYL SULFIDES AND PROCESSES

[75] Inventors: William J. Evers, Middletown; Howard H. Heinsohn, Jr., Hazlet; Bernard J. Mayers, Cliffwood, all of N.J.

[73] Assignee: International Flavors & Fragrances Inc., New York, N.Y.

[ * ] Notice: The portion of the term of this patent subsequent to May 30, 1992, has been disclaimed.

[22] Filed: Sept. 15, 1976

[21] Appl. No.: 723,531

Related U.S. Application Data

[63] Continuation-in-part of Ser. No. 639,754, Dec. 11, 1975, abandoned, which is a continuation-in-part of Ser. No. 551,150, Feb. 19, 1975, abandoned.

[52] U.S. Cl. ............................................. 426/535
[51] Int. Cl.$^2$ ....................................... A23L 1/231
[58] Field of Search .................................... 426/535

[56] References Cited

UNITED STATES PATENTS

| | | | |
|---|---|---|---|
| 3,666,495 | 5/1972 | Evers | 426/535 |
| 3,778,518 | 12/1973 | Copier et al. | 426/535 |
| 3,836,563 | 9/1974 | Evers et al. | 426/535 UX |
| 3,873,732 | 3/1975 | Evers et al. | 426/535 UX |
| 3,982,038 | 9/1976 | Evers et al. | 426/535 |

FOREIGN PATENTS OR APPLICATIONS 1,283,912   8/1972   United Kingdom   ............... 426/535

*Primary Examiner*—Joseph M. Golian
*Attorney, Agent, or Firm*—Arthur L. Liberman; Harold Haidt; Franklin D. Wolffe

[57] ABSTRACT

3-Furyl alkyl sulfides having the formula:

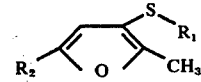

wherein $R_1$ is $C_1-C_5$ lower alkyl and $R_2$ is selected from the group consisting of hydrogen and methyl, are described as being useful in altering, modifying or enhancing the organoleptic properties of foodstuffs.

6 Claims, No Drawings

FOODSTUFF FLAVOR COMPOSITIONS COMPRISING 3-FURYL ALKYL SULFIDES AND PROCESSES

This application is a continuation-in-part of U.S. application for Letters Patent Ser. No. 639,754, filed on Dec. 11, 1975, now abandoned, which, in turn, is a continuation-in-part of U.S. application for Letters Patent Ser. No. 551,150, filed on Feb. 19, 1975, now abandoned.

BACKGROUND OF THE INVENTION

The present invention relates to novel uses in foodstuffs and in foodstuff flavors of 3-furyl alkyl sulfides.

Artificial flavoring agents for foodstuffs have received increasing attention in recent years. In many areas, such food flavoring agents are preferred over natural flavoring agents at least in part because of the uniform flavor that may be so obtained. For example, natural food flavoring agents such as extracts, essences, concentrates and the like are often subject to wide variation due to changes in the quality, type and treatment of the raw materials. Such variation can be reflected in the end product and results in unreliable flavor characteristics and uncertainty as to consumer acceptance and cost. Additionally, the presence of the natural product in the ultimate food may be undesirable because of increased tendency to spoil. This is particularly troublesome in convenience and snack food usage where such products as dips, soups, chips, prepared dinners, canned foods, sauces, gravies and the like are apt to be stored by the consumer for some time prior to use.

The fundamental problem in preparing artificial flavoring agents is that of achieving as nearly as possible a true flavor reproduction. This generally proves to be a difficult task since the mechanism for flavor development in many foods is not understood. This is notable in products having meaty and roasted flavor characteristics.

Reproduction of sweet, meaty nutty, cereal-like, baked bread, liver-like, hydrolyzed protein-like, hazelnut, and pecan-like flavors and aromas has been the subject of the long and continuing search by those engaged in the production of foodstuffs. The severe storage of foods, especially protein foods, in many parts of the world has given rise to the need for utilizing non-meat sources of proteins and making such proteins as palatable and as meat-like as possible. Hence, materials which will closely simulate or exactly reproduce the flavor and aroma of roasted meat products and liver products are required.

Moreover, there are a great many meat containing or meat based food presently distributed in a preserved form. Examples being condensed soups, dry-soup mixes, dry meat, freeze-dried or lyophilized meats, packaged gravies and the like. While these products contain mat or meat extracts, the fragrance, taste and other organoleptic factors are very often impaired by the processing operation and it is desirable to supplement or enhance the flavors of these preserved foods with versatile materials which have either sweet, meaty, nutty, cereal-like, baked bread, liver-like, hydrolyzed vegetable protein-like, hazelnut or pecan-like aroma and taste nuances.

U.S. Pat. No. 3,666,495 has to do with certain furan derivatives having desirable meat, roast meat and fragrance and flavor notes. Among the furan derivatives disclosed in said patent are methyl (2-methyl-3-furyl) trisulfide obtained by the reaction of 2-methyl-3-furan thiol with methyl disulfur chloride at a temperature of from −60° C to 0° C, and methyl (2-methyl-3-furyl) disulfide obtained by reacting 2-methyl-3-furan thiol with methane sulfenyl chloride.

The organoleptic properties of such 3-furyl alkyl disulfides are different in flavor character and intensity from the organoleptic properties of 3-furyl alkyl sulfides of our invention.

U.S. Pat. No. 3,836,563 issued on Sept. 17, 1974 broadly discloses 3-furyl alkyl sulfides having the structure:

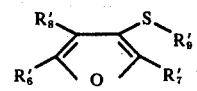

wherein $R_9'$ may be alkyl such as methyl, ethyl, n-propyl, isopropyl, n-butyl, isobutyl, n-hexyl, n-octyl and n-nonyl (See Col. 4, lines 10–18), and $R_7'$, $R_8'$ and $R_9'$ are either hydrogen or alkyl. However, U.S. Pat. No. 3,836,563 does not contain claims drawn to such compounds or uses thereof and the subject matter claimed herein was invented by us prior to Aug. 7, 1973, the filing data of U.S. Pat. No. 3,836,563.

Danyushevskii, et al. *J. Org. Chem.* U.S.S.R., 6, 866–870 (1970) (Abstracted in Chem. Abstracts 70, 68020 (1969)) discloses compounds having the structure:

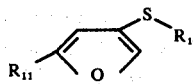

(wherein $R_{10}$ and $R_{11}$ are lower alkyl) without describing any organoleptic properties thereof.

THE INVENTION

The present invention provides 3-furyl alkyl sulfides for altering, modifying or enhancing the organoleptic properties of foodstuffs. Briefly, the novel compounds are 3-furyl alkyl sulfides having the formula:

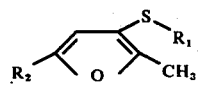

wherein $R_1$ is $C_1$–$C_5$ lower alkyl and $R_2$ is selected from the group consisting of hydrogen and methyl.

Thus, for example, 3-furyl alkyl sulfides contemplated within the scope of our invention are:

| 3-Furyl Alkyl Sulfide Compounds | Structure |
| --- | --- |
| (2-methyl-3-furyl) methyl sulfide | 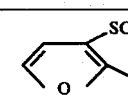 |
| (2,5-dimethyl-3-furyl) propyl sulfide | 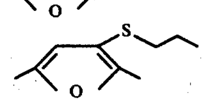 |
| isoamyl(2-methyl-3-furyl) sulfide | 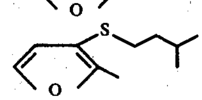 |

The 3-furyl alkyl sulfides of our invention can be prepared by a process comprising the steps of:

i. Providing a 2-ene-1,4-dione having the structure:

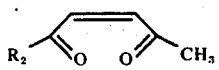

ii. Intimately admixing said 2-ene-1,4-dione with an alkane thiol having the formula $R_1SH$ thereby providing a substituted or unsubstituted 2-thia substituted 1,4-dione having the structure:

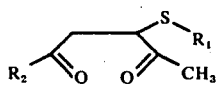

iii. Cyclizing said 2-thia substituted 1,4-dione to form a substituted or unsubstituted 3-furyl alkyl sulfide having the formula:

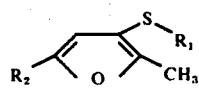

wherein $R_1$ is $C_1$–$C_5$ alkyl and $R_2$ and $R_3$ are each hydrogen or methyl, at least one of $R_2$ and $R_3$ being methyl. $R_2$ may be hydrogen in the event that in step (ii) the 2-ene-1,4 dione is admixed with the alkane thiol having the formula $R_1SH$ in the presence of an organic base such as piperidine, pyridine, triethyl amine, quinoline or alpha-picoline or a mixture thereof.

The 2-ene-1,4-dione may be prepared by hydrolysis of a 2,5-dialkoxy-2,5-dihydrofuran. The resulting material will be in the case of starting with 2,5-dimethoxy-2,5-dimethyl-2,5-dihydrofuran, cis-3-hexen-2,5-dione.

The resulting 2-ene-1,4-dione is then reacted with an alkane thiol having the formula $R_1SH$ wherein $R_1$ is lower alkyl.

Examples of such alkane thiols are:
Ethane thiol;
1-Propane thiol;
Methane thiol;
1-Pentane thiol;
2-Pentane thiol;
2-Propane thiol;
1-Butane thiol;
2-Butane thiol;
2-Methyl-1-propane thiol;
2-Methyl-2-propane thiol;
3-Methyl-1-butane thiol;
2-Methyl-1-butane thiol;
2-Methyl-2-butane thiol; and
2-Methyl-3-butane thiol Examples of useful organic bases are piperidine, pyridine, quinoline, triethyl amine and alpha-picoline. In place of such organic bases, radical initiators may be used such as benzoyl peroxide or azobisisobutyl nitrile. The reaction may be carried out in a solvent such as water or an ether such as diethyl ether or a hydrocarbon such as benzene or hexane or cyclohexane. The reaction may also be carried out without the use of a solvent. The reaction may be carried out under reflux conditions although temperatures varying from 0° up to 60° C are suitable and will give rise to commercially suitable yields. When the reaction is carried out with highly volatile reactants, e.g., methyl mercaptan, higher pressures than atmospheric pressures are preferred, e.g., three atmospheres pressure.

The aforementioned 2-thia substituted-1,4-diones are then cyclized to form substituted or unsubstituted 3-thiafurans according to the following reaction:

wherein $R_1$ and $R_2$ are defined as above. The resulting 3-furyl alkyl sulfides are then used for their organoleptic properties.

The cyclization of the 2-thia substituted-1,4-dione is carried out in the presence of a cyclization agent, preferably, isopropenyl acetate. The cyclization is also carried out in the presence of such a catalyst as concentrated sulfuric acid, zinc chloride, boron trifluoride, aluminum trichloride, and para-toluene sulfonic acid, each of these being acid catalysts. Preferably, the ratio of isopropenyl acetate to 2-thia substituted-1,4-dione is 4 or 5:1. The ratio of acid catalyst to isopropenyl acetate is from 0.001 up to 0.05 (mole ratio). The cyclization reaction may be run at temperatures of between 25° C up to reflux at atmospheric pressure (96° C). Still greater reflux temperatures may be used if the pressure is greater than atmospheric. Furthermore, in place of isopropenyl acetate as a cyclization agent, acetic anhydride or propionic anhydride to 2-thia substituted-1,4-dione are preferably 4 to 5:1 (mole ratio).

The reaction product is then purified by appropriate extraction and distillation techniques.

The 3-furyl alkyl sulfides of our invention can also be prepared by reacting 3-furan thiols, e.g., 2-methyl-3-furan thiol with an appropriate alkyl halide (i) in the presence of a base such as an alkali metal alkoxide (e.g., sodium methoxide); (ii) at a temperature in the range of 15°–100° C and (iii) in a suitable inert compatible solvent, e.g., an anhydrous lower alkanol such as anhydrous methanol, ethanol or isopropanol. Thus, for example, methyl iodide, when reacted with 2-methyl-3-furan thiol in anhydrous methanol in the presence of sodium methoxide at a temperature of 24° C will yield (2-methyl-3-furyl) methyl sulfide. Thus, as a further example, sodium methylate is reacted with 2-methyl-3-furan thiol to form the corresponding mercaptide which is, in turn, reacted with 1-bromo-3-methyl butane at reflux temperature and 1 atmosphere pressure thereby forming isoamyl (2-methyl-3-furyl) sulfide.

The following compounds of our invention produced using the above processes have useful organoleptic properties giving rise to their use as foodstuff flavors as set forth in an illustrative manner in the following table:

TABLE I

| 3-Furyl Alkyl Sulfide Compound | Structure | Flavor Properties |
|---|---|---|
| (2-methyl-3-furyl) methyl sulfide | 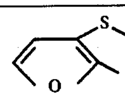 | Sweet, meat extract cereal-like flavor with broth-like and nutty notes, and a sweet, brothy aroma. |
| (2,5-dimethyl-3-furyl)propyl sulfide | 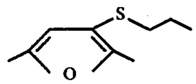 | Oniony, sulfury aroma and pleasant meaty, sulfury taste. |
| isoamyl(2-methyl-3-furyl) sulfide | 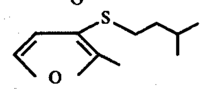 | Sweet, baked bread meaty aroma with liver-like nuances and green, sweet, "hydrolyzed vegetable protein" like, yeast-like flavor with baked bread, hazel-nut, liver, sulfury and pecan nuances. |

The 3-furyl alkyl sulfides according to the present invention can be used to alter, vary, fortify, modify, enhance, or otherwise improve the organoleptic properties, including flavor and/or aroma, of a wide variety of materials which are ingested, consumed or otherwise organoleptically sensed.

The terms "alter" and "modify" in their various forms will be understood herein to mean the supplying or imparting a flavor character or note to an otherwise bland, relatively tasteless substance, or augmenting an existing flavor characteristic where the natural flavor is deficient in some regard, or supplementing the existing flavor or aroma impression to modify the organoleptic character. The materials which are so altered or modified are generally referred to herein as consumable materials.

The term "enhance" as used herein is intended to mean the intensification of a flavor or aroma characteristic, note or nuance without the modification of the quality thereof. Thus "enhancement" of a flavor or aroma means that the enhancement agent does not add any additional flavor note or nuance, in the concentration utilized (based upon the weight of foodstuff in which it is utilized).

Such 3-furyl alkyl sulfides of this invention are accordingly useful in flavoring compositions. Flavoring compositions are herein taken to mean those which contribute a part of the overall flavor impression by supplementing or fortifying a natural or artificial flavor in a material, as well as those which supply substantially all the flavor and/or aroma to a consumable article.

The term "foodstuff" as used herein includes both solid and liquid ingestible materials for man or animals, which materials usually do, but need not, have nutritional value. Thus, foodstuffs includes meats, gravies, soups and convenience food, vegetables, snack foods, dog and cat foods, other veterinary products, and the like.

When the 3-furyl alkyl sulfides according to this invention are used in a food flavoring composition, they can be combined with conventional flavoring materials or adjuvants. Such co-ingredients or flavoring adjuvants are well known in the art for such use and have been extensively described in the literature. Such adjuvant material is required (1) to be substantially non-reactive with the 3-furyl alkyl sulfides used in our invention particularly whereby unwanted detrimental organoleptic properties are not created in the overall organoleptic impression of the ultimate foodstuff used; (2) to be, taken alone or taken together with other materials used in conjunction therewith, ingestibly acceptable from an aesthetic standpoint and from an organoleptic standpoint; (3) to be non-toxic and (4) to be otherwise non-deleterious. Apart from these requirements, conventional materials can be used and broadly include other flavor materials, vehicles, stabilizers, thickeners, surface active agents, conditioners, and flavor intensifiers.

Examples of preferred co-flavoring adjuvants are:
Methyl thiazole alcohol (4-methyl-5beta-hydroxyethyl thiazole);
2-Methyl butanethiol;
4-Mercapto-2-butanone;
3-Mercapto-2-pentanone;
1-Mercapto-2-propanone;
Benzaldehyde;
Furfural;
Furfuryl alcohol;
2-Mercapto propionic acid;
2-Methylfuran-3-thiol;
2-Methyldihydrofuran-3-thiol;
2-Methyltetrahydrofuran-3-thiol;
2-Ethylfuran-3-thiol;
2-Ethyldihydrofuran-3-thiol;
2-Ethyltetrahydrofuran-3-thiol;
2-Propylfuran-3-thiol;
2-Isopropylfuran-3-thiol;
2-Isopropyldihydrofuran-3-thiol;
2-Isopropyltetrahydrofuran-3-thiol;
2-Propyldihydrofuran-3-thiol;
2,5-Dimethylfuran-3-thiol;
2,5-Dimethyldihydrofuran-3-thiol;
2,5-Dimethyltetrahydrofuran-3-thiol;
2,5-Diethylfuran-3-thiol;
2,5-Diethyldihydrofuran-3-thiol;
2,5-Diethyltetrahydrofuran-3-thiol;
2-Ethyl-5-methylfuran-3-thiol;
2-Methyl-5-ethylfuran-3-thiol;
2-Ethyl-5-methyldihydrofuran-3-thiol;
2-Ethyl-5-methyltetrahydrofuran-3-thiol;
2,5-Dipropylfuran-3-thiol;
2,5-Diisopropylfuran-3-thiol;
5-Isopropyl-2-methylfuran-3-thiol;
2-Butylfuran-3-thiol;
2-Ethyl-5-propyltetrahydrofuran-3-thiol;
Bis(2-methyl-3-furyl) sulfide;
Bis(2-methyl-3-furyl) disulfide;
Bis(2-ethyl-3-furyl) sulfide;
Bis(2-ethyl-3-furyl) disulfide;
Bis(2,5-dimethyl-3-furyl) sulfide;
Bis(2,5-dimethyl-3-furyl) disulfide;
Bis(2-methyl-3-dihydrofuryl) sulfide;
Bis(2-methyl-3-tetrahydrofuryl) sulfide;
Bis(2-methyl-3-tetrahydrofuryl) disulfide;
Bis(2-methyl-3-dihydrofuryl) disulfide;
Bis(2,5-diethyl-3-furyl) sulfide;
Bis(2-ethyl-5-methyl-3-furyl) disulfide;
Bis(2,5-diethyl-3-furyl) disulfide;
Bis(2,5-dipropyl-3-furyl) disulfide
Bis(2,5-dipropyl-3-furyl) sulfide;
Bis(2,5-dibutyl-3-furyl) disulfide;
Bis(5-ethyl-2-methyl-3-dihydrofuryl) disulfide;
Bis(2-isopropyl-3-furyl) sulfide;
Bis(2-isopropyl-3-furyl) disulfide;
Bis(2-isopropyl-3-dihydrofuryl) sulfide;
Bis(2-isopropyl-3-tetrahydrofuryl) disulfide;

Alkyl pyrazine;
Methyl pyrazine;
2-Ethyl-3-methyl pyrazine;
Tetramethyl pyrazine;
Dipropyl disulfide;
Methyl benzyl disulfide;
Alkyl thiophenes;
2-Butyl thiophene;
2,3-Dimethyl thiophene;
5-Methyl furfural;
Acetyl furan;
2,4-Decadienal;
Guiacol;
Phenyl acetaldehyde;
δ-Decalactone;
d-Limonene;
Acetoin;
Amyl acetate;
Maltol;
Ethyl butyrate;
Levulinic acid;
Piperonal;
Ethyl acetate;
n-Octanal;
n-Pentanal;
Hexanal;
Diacetyl;
Monosodium glutamate;
Sulfur-containing amino acids;
Crysteine;
Hydrolyzed vegetable protein;
Hydrolyzed fish protein; and
Tetramethyl pyrazine The 3-furyl alkyl sulfides or the compositions incorporating them, as mentioned above, can be combined with one or more vehicles or carriers for adding them to the particular product. Vehicles can be edible or otherwise suitable materials such as ethyl alcohol, propylene glycol, water and the like. Carriers include materials such as gum arabic, carrageenan, other gums and the like. The 3-furyl alkyl sulfides according to this invention can be incorporated with the carriers by conventional means such as spray-drying, drum-drying, and the like. Such carriers can also include materials for coacervating the 3-furyl alkyl sulfides (and other flavoring ingredients, as present) to provide encapsulated products. When the carrier is an emulsion the flavoring composition can also contain emulsifiers such as mono- and diglycerides of fatty acids and the like. With these carriers or vehicles, the desired physical form of the composition can be prepared.

The quantity of 3-furyl alkyl sulfides utilized should be sufficient to impart the desired flavor characteristic to the product, but on the other hand, the use of an excessive amount of the derivative is not only wasteful and uneconomical, but in some instances too large a quantity may unbalance the flavor or other organoleptic properties of the product consumed. The quantity used will vary depending upon the ultimate foodstuff; the amount and type of flavor initially present in the foodstuff; the further process or treatment steps to which the foodstuff will be subjected; regional and other preference factors; the type of storage, if any, to which the product will be subjected; and the preconsumption treatment, such as baking, frying, and so on, given to the product by the ultimate consumer. Accordingly, the terminology "effective amount" and "sufficient amount" is understood in the context of the present invention to be quantitatively adequate to alter the flavor of the foodstuff.

It is accordingly preferred that the ultimate compositions contain from about 0.0005 parts per million (ppm) to about 250 ppm of 3-furyl alkyl sulfides. More particularly, in food compositions, it is desirable to use from about 0.0005 ppm to 100 ppm to enhancing flavors and in certain preferred embodiments of the invention, from about 0.2 to 50 ppm of the derivatives are included to add positive flavors to the finished product. All parts, proportions, percentages, and ratios herein are by weight unless otherwise indicated.

The amount of 3-furyl alkyl sulfides of our invention to be utilized in flavoring compositions can be varied over a wide range to the foodstuff. Thus, amounts of one or more derivatives according to the present invention of from about 2 ppm up to 80 or 90 percent of the total flavoring composition can be incorporated in such compositions. It is generally found to be desirable to include from about 10 ppm up to about 20 percent of the 3-furyl alkyl sulfide in such compositions.

The following examples are given to illustrate embodiments of the invention as it is preferably preferred to practice it. It will be understood that these examples are illustrative and the invention is not to be considered as restricted thereto except as indicated in the appended claims.

EXAMPLE I

Preparation of (2-Methyl-3-Furyl) Methyl Sulfide

Into a 50 ml round bottom flask equipped with 10 ml addition funnel, magnetic stirrer, nitrogen inlet tube, Y-tube, CaCl₂ drying tube and thermometer, 7.5 ml anhydrous methanol is added. 0.474 Grams (0.00878 moles) NaOCH₃ is then charged into the methanol with stirring. The reaction mass is then cooled to 24° C and a solution of 1.0 g (0.00878 moles) of 2-methyl-3-furan thiol in 7.5 ml anhydrous methanol is added to the reaction mass under a blanket of nitrogen.

Over a period of 15 minutes, a solution of 1.248 g (0.00878 moles) of methyl iodide in 4 ml of anhydrous methanol is added to the reaction mass. After stirring 30 minutes, water (30 ml) is added and the pH of the resulting mixture is adjusted to 5 with 4% hydrochloric acid. The mixture is then extracted twice with hexane (16 and 15 ml). The combined n-hexane extracts are gravity-filtered and then concentrated to 2 ml.

GLC analysis of the concentrate shows the presence of the following compounds.

| Peak A | 93.3% | (structure: furan with SCH₃) |
|---|---|---|
| Peak B | 5.4% | (structure: furan with SH) |

Peak A, the desired product, is isolated by preparative GLC.

Mass spectral analysis, infrared analysis and NMR analysis confirm the structure as being:

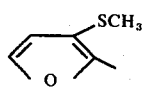

This material has a sweet, meat extract cereal-like flavor with broth-like and nutty notes, and a sweet, brothy aroma.

EXAMPLE II

Preparation of Isoamyl (2-Methyl-3-Furyl) Sulfide

Reaction:

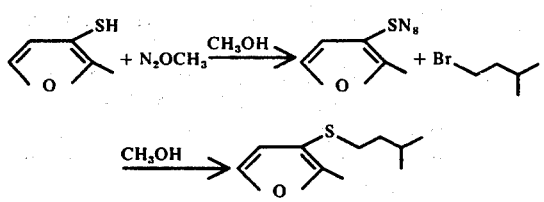

To a solution of 0.27 grams (0.005 moles) of sodium methylate in 3 ml of methanol is added a solution of 0.005 moles (0.57 grams) of 2-methyl-3-furanthiol dissolved in 3 ml of methanol. The resulting yellow solution is stirred for a period of 10 minutes and then 1-bromo-3-methyl butane (isoamyl bromide) (0.005 moles) in 1 ml methanol is added dropwise over a 2-minute period to the reaction mass. The reaction mass is then refluxed for a period of 9 hours at 63° C.

The reaction mass is then cooled to 25° C and 10 ml of water is added. After neutralization to pH 6 with 4% hydrochloric acid, 10 ml of n-hexane is added and the organic phase separated. The aqueous layer is extracted with 6 ml of n-hexane, and the organic phase and the hexane extracts are combined and washed with saturated sodium chloride. The organic layer is then dried over anhydrous sodium sulfate, concentrated to give 0.60 g of crude oil. A sample of isoamyl (2-methyl-3-furyl) sulfide is isolated from the oil using gas-liquid chromatography apparatus (conditions: 8 inches × ¼ inch column, 25% SE-30).

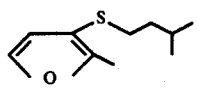

The structure is confirmed by mass spectral analysis, NMR analysis and IR analysis.

Mass spectral analysis: m/e (in decreasing intensity): 114, 43, 184 (molecular ion), 27, 41, 113, 45

This material has a sweet, baked bread, meaty aroma with liver nuances and a green, sweet, hydrolyzed vegetable protein-like, yeast flavor with baked bread, hazelnut, liver, sulfury and pecan nuances.

EXAMPLE III

The following ingredients are refluxed for four hours:

| Ingredient | Parts by Weight |
|---|---|
| L-Cysteine hydrochloride | 0.9 |
| Carbohydrate-free vegetable protein hydrolysate | 30.9 |
| Thiamine hydrochloride | 0.9 |
| Water | 67.30 |

The resulting mixture is then aged for 3 days and an aliquot portion is withdrawn and dried. Based on the weight of the dry solid obtained, sufficient gum arabic is added to the batch to provide a composition containing one part by weight of gum arabic. The composition is then spray-dried.

Methyl(2-methyl-3-furyl) sulfide is added to the spray-dried material to a concentration of 10 ppm.

The resulting material has an excellent unique sweet meat flavor.

EXAMPLE IV

A beef liver gravy is made by formulating a composition in the amounts indicated:

| Ingredient | Parts by Weight |
|---|---|
| Cornstarch | 10.50 |
| The final product produced according to Example IV | 3.00 |
| Caramel color | .30 |
| Garlic powder | .05 |
| White pepper | .05 |
| Salt | 1.92 |
| Monosodium glutamate | .20 |

To one unit of gravy flavor concentrate, eight ounces of water is added, and the mixture is stirred thoroughly to disperse the ingredients brought to a boil, simmered for 1 minute and served. This "meatless" gravy exhibits an excellent unique sweet meat flavor.

EXAMPLE V

Use of (2-Methyl-3-Furyl) Methyl Sulfide (2-Methyl-3-furyl) methyl sulfide is added to beef broth prepared from a commercial dried mixture and 250 ml hot water to yield a final concentration of 3 ppm of sulfide. The (2-methyl-3-furyl) methyl sulfide increases the sweet meat and nutty character and enhances the broth-like note. The resultant beef broth has an improved more blended meaty flavor than does the unflavored beef broth.

EXAMPLE VI

The following formulation is prepared:

| Ingredient | Parts by Weight |
|---|---|
| Liquid hydrolyzed vegetable protein | 90 |
| 4-Methyl-beta-hydroxy-ethyl-thiazole | 5 |
| Tetrahydro thiophene-3-one | 1 |
| Furfuryl mercaptan | 0.01 |
| 2-Nonenal | 0.50 |
| Difurfuryl disulfide | .49 |
| Dimethyl sulfide | 0.50 |
| Methyl mercaptan | 0.50 |
| (2,5-Dimethyl-3-furyl) propyl sulfide prepared according to the process of Example II | 2.00 |

The (2,5-dimethyl-3-furyl) propyl sulfide has a sweet blending effect, imparting a meaty oniony taste leaning towards an "Irish Stew" taste effect. This chemical helps reduce the typical hydrolyzed vegetable protein taste and ties in and rounds up the other meat-like chemicals in the formula.

EXAMPLE VII

Use of (2,5-Dimethyl-3-Furyl) Propyl Sulfide (2,5-Dimethyl-3-furyl) propyl sulfide is added to beef broth prepared from a commercial dried mixture and 250 ml hot water to yield a final concentration of 4 ppm of sulfide. The (2,5-dimethyl-3-furyl) sulfide imparts an "Irish Stew" character and enhances the oniony note. The resultant beef broth has an improved more blended meaty flavor than does the unflavored beef broth.

EXAMPLE VIII

The following ground sausage mixture is prepared:

| Ingredient | Parts by Weight |
|---|---|
| Ground Beef | 200 |
| Beef suet | 120 |
| Ice/NaCl (50:50 mixture) | 200 |
| Potato flour | 100 |
| Anhydrous bread crumbs | 140 |
| Dry milk powder | 20 |
| Standard spice flavor containing: | 10 |
| Oil of cumin | 1.6 |
| Oil of mustard | 3.3 |
| Oil of celery | 3.3 |
| Oil of ginger | 5.2 |
| Oil of cloves | 14.3 |
| Oil of coriander | 17.6 |
| Oil of pimenta berries | 22.0 |
| Oil of black pepper | 43.0 |
| Oleoresin capsicum | 373.0 |
| Oil of nutmeg | 500.0 | to the above mixture 0.02% by weight of the following mixture is added:

| Ingredient | Parts by Weight |
|---|---|
| Isoamyl(2-methyl-3-furyl) sulfide prepared according to Example III | 5 |
| Ethyl alcohol | 95 |

The resulting mixture is then formed into a sausage and encased in the usual manner. The encased sausage is heated in water at a temperature of 160°–180° F for a period of 2 hours. This sausage has a sweet liver-taste reminiscent of the taste of sausage made with natural liver.

EXAMPLE IX

A mixture of 8.8 g of cysteine-hydrochloride, 8.8 g of thiamine hydrochloride and 309.4 g of carbohydrate-free vegetable protein hydrolysate is brought to a standard weight of 1000 grams by the addition of water and adjusted to 4.75 pH with acid or base as required. This mixture is then boiled under reflux conditions at atmospheric pressure for four hours and allowed to cool.

After the mixture is allowed to cool, 0.001 g of isoamyl(2-methyl-3-furyl) sulfide prepared according to Example II is added thereto. The resulting mixture thus obtained has an excellent unique sweet, livery, meaty flavor with baked bread and hazelnut nuances.

EXAMPLE X

Use of Isoamyl (2-Methyl-3-Furyl) Sulfide

Isoamyl (2-methyl-3-furyl) sulfide is added to beef broth prepared from a commercial dried mixture and 250 ml hot water to yield a sulfide concentration of 2 ppm. The isoamyl (2-methyl-3-furyl) sulfide increases the sweet meat and livery character and imparts a nutty note. The resultant beef broth has an improved more blended meaty flavor than does the unflavored beef broth.

What is claimed is:
1. A process for augmenting or enhancing the nutty notes of a foodstuff having a meaty flavor comprising the step of adding to said foodstuff from about 0.0005 ppm up to about 250 ppm of a 3-furyl alkyl sulfide compound having the structure:

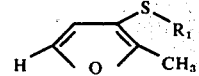

wherein $R_1$ is selected from the group consisting of methyl and 3-methyl-1-butyl.

2. The process of claim 1 wherein, in the structure of the 3-furyl alkyl sulfide compound, $R_1$ is methyl.

3. The process of claim 1 wherein, in the structure of the 3-furyl alkyl sulfide compound, $R_1$ is 3-methyl-1-butyl.

4. A food flavor composition useful in augmenting or enhancing the nutty notes of a foodstuff having a meaty flavor consisting essentially of (i) from about 2 ppm up to 90% by weight of a 3-furyl alkyl sulfide compound having the structure:

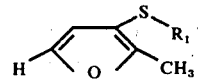

wherein $R_1$ is selected from the group consisting of methyl and 3-methyl-1-butyl, the remainder of said composition being (ii) one or more adjuvant flavoring materials which are organoleptically compatible and non-reactive with said 3-furyl alkyl sulfide, said adjuvant flavoring material being at least one of:
4-methyl-5-beta-hydroxyethyl thiazole;
2-methyl butanethiol;
4-mercapto-2-butanone;
3-mercapto-2-pentanone;
1-mercapto-2-propanone;
benzaldehyde;
furfural;
furfuryl alcohol;
2-mercapto propionic acid;
2-methylfuran-3-thiol;
2-methyldihydrofuran-3-thiol;
2-methyltetrahydrofuran-3-thiol;
2-ethylfuran-3-thiol;
2-ethyldihydrofuran-3-thiol;
2-ethyltetrahydrofuran-3-thiol;
2-propylfuran-3-thiol;
2-isopropylfuran-3-thiol;
2-isopropyldihydrofuran- 3-thiol;
2-isopropyltetrahydrofuran-3-thiol;
2-propyldihydrofuran-3-thiol;
2,5-dimethylfuran-3-thiol;
2,5-dimethyldihydrofuran-3-thiol;
2,5-dimethyltetrahydrofuran-3-thiol;
2,5-diethylfuran-3-thiol;
2,5-diethyldihydrofuran-3-thiol;
2,5-diethyltetrahydrofuran-3-thiol;
2-ethyl-5-methylfuran-3-thiol;
2-methyl-5-ethylfuran-3-thiol;
2-ethyl-5-methyldihydrofuran-3-thiol;
2-ethyl-5-methyltetrahydrofuran-3-thiol;
2,5-dipropylfuran-3-thiol;
2,5-diisopropylfuran-3-thiol;
5-isopropyl-2-methylfuran-3-thiol;
2-butylfuran-3-thiol;
2-ethyl-5-propyltetrahydrofuran-3-thiol;

bis(2-methyl-3-furyl) sulfide;
bis(2-methyl-3-furyl) disulfide;
bis(2-ethyl-3-furyl) sulfide;
bis(2-ethyl-3-furyl) disulfide;
bis(2,5-dimethyl-3-furyl) sulfide;
bis(2,5-dimethyl-3-furyl) disulfide;
bis(2-methyl-3-dihydrofuryl) sulfide;
bis(2-methyl-3-tetrahydrofuryl) sulfide;
bis(2-methyl-3-tetrahydrofuryl) disulfide;
bis(2-methyl-3-dihydrofuryl) disulfide;
bis(2,5-diethyl-3-dihydrofuryl) sulfide;
bis(2,5-diethyl-3-furyl) sulfide;
bis(2-ethyl-5-methyl-3-furyl) disulfide;
bis(2,5-diethyl-3-furyl) disulfide;
bis(2,5-dipropyl-3-furyl) disulfide;
bis(2,5-dipropyl-3-furyl) sulfide;
bis(2,5-dibutyl-3-furyl) disulfide;
bis(5-ethyl-2-methyl-3-dihydrofuryl) disulfide;
bis(2-isopropyl-3-furyl) sulfide;
bis(2-isopropyl-3-furyl) disulfide;
bis(2-isopropyl-3-dihydrofuryl) sulfide;
bis(2-isopropyl-3-tetrahydrofuryl) disulfide;
alkyl pyrazine;
methyl pyrazine;
2-ethyl-3-methyl pyrazine;
tetramethyl pyrazine;
dipropyl disulfide;
methyl benzyl disulfide;
alkyl thiophenes;
2-butyl thiophene;
2,3-dimethyl thiophene;
5-methyl furfural;
acetyl furan;
2,4-decadienal;
guiacol;
phenyl acetaldehyde;
δ-decalactone;
d-limonene;
acetoin;
amyl acetate;
maltol;
ethyl butyrate;
levulinic acid;
piperonal;
ethyl acetate;
n-octanal;
n-pentanal;
hexanal;
diacetyl;
monosodium glutamate;
sulfur-containing amino acids;
cysteine;
hydrolyzed vegetable protein;
hydrolyzed fish protein; and
tetramethyl pyrazine.

5. The food flavor composition of claim 4 wherein, in the structure of the 3-furyl alkyl sulfide compound, $R_1$ is methyl.

6. The composition of claim 4 wherein, in the 3-furyl alkyl sulfide compound, $R_1$ is 3-methyl-1-butyl.

* * * * *

UNITED STATES PATENT AND TRADEMARK OFFICE
CERTIFICATE OF CORRECTION

PATENT NO. : 4,031,256

DATED : June 21, 1977

INVENTOR(S) : William J. Evers; Howard H. Heinsohn, Jr. Bernard J. Mayers

It is certified that error appears in the above-identified patent and that said Letters Patent are hereby corrected as shown below:

Column 1, line 58: "mat" should read --- meat ---

Column 6, line 11: "(4-methyl-5beta-hydrox-" should read --- (4-methyl-5-beta-hydrox- ---

Column 9, line 10: The reaction:

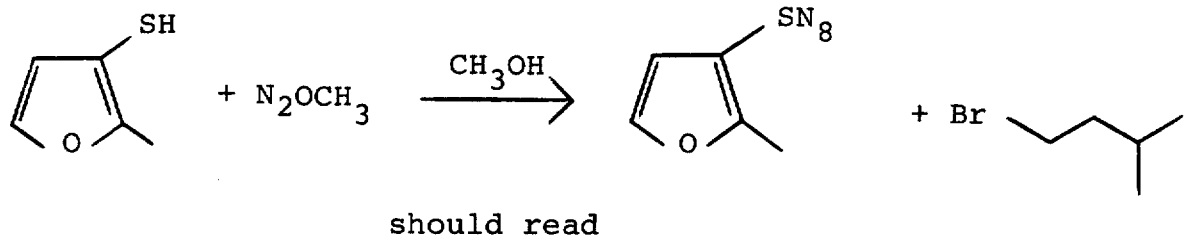

should read

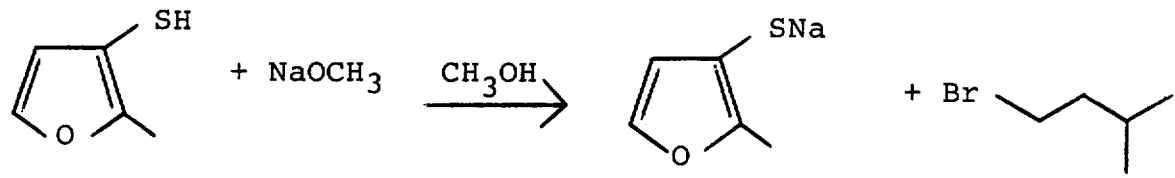

Column 10, line 16: "Example IV" should read --- Example III ---

UNITED STATES PATENT OFFICE
CERTIFICATE OF CORRECTION

Patent No. 4,031,256     Dated June 21, 1977

Inventor(s) William J. Evers; Howard H. Heinsohn, Jr.; Bernard J. Mayers

It is certified that error appears in the above-identified patent and that said Letters Patent are hereby corrected as shown below:

Column 10, lines 53-54: "prepared according to Example II" should be deleted

Column 11, line 32: "Example III" should read
--- Example II ---

Signed and Sealed this

Twenty-seventh Day of June 1978

[SEAL]

Attest:

RUTH C. MASON
Attesting Officer

DONALD W. BANNER
Commissioner of Patents and Trademarks